United States Patent [19]
Anderson et al.

[11] Patent Number: 5,985,655
[45] Date of Patent: Nov. 16, 1999

[54] TARGETABLE VECTOR PARTICLES

[75] Inventors: W. French Anderson, San Marino, Calif.; Leon F. Baltrucki, Rockville; James M. Mason, Laurel, both of Md.

[73] Assignee: The United States of America as represented by the Department of Health and Human Sevices, Washington, D.C.

[21] Appl. No.: 08/484,126

[22] Filed: Jun. 7, 1995

Related U.S. Application Data

[63] Continuation of application No. 08/326,347, Oct. 20, 1994, abandoned, which is a continuation of application No. 07/973,307, Nov. 9, 1992, abandoned.

[51] Int. Cl.⁶ .................................................. C12N 15/63
[52] U.S. Cl. ........................................ 435/320.1; 435/325
[58] Field of Search ................................ 435/320.1, 239, 435/235.1, 172.1, 240.2; 424/93.2, 424, 425; 514/120

[56] References Cited

U.S. PATENT DOCUMENTS

| | | | |
|---|---|---|---|
| 5,328,470 | 7/1994 | Nabel et al. | 604/101 |
| 5,354,674 | 10/1994 | Hodgson | 435/172.3 |
| 5,512,421 | 4/1996 | Burns et al. | 435/320.1 |
| 5,591,624 | 1/1997 | Barber et al. . | |

FOREIGN PATENT DOCUMENTS

| | | |
|---|---|---|
| 0 334 301 | 9/1989 | European Pat. Off. . |
| 02805 | 3/1991 | WIPO . |
| WO92/06180 | 4/1992 | WIPO . |
| WO92/14829 | 9/1992 | WIPO . |
| WO92/20316 | 11/1992 | WIPO . |
| WO93/00103 | 1/1993 | WIPO . |
| WO93/14188 | 7/1993 | WIPO . |
| WO93/20221 | 10/1993 | WIPO . |
| WO93/25234 | 12/1993 | WIPO . |

OTHER PUBLICATIONS

Goud et al. Virology. vol. 163, pp. 251–254, 1988.
Maddon et al. Cell. vol. 47, pp. 333–348, 1986.
Jolly, D. Cancer Gene Therapy. vol. 1, No. 1, pp. 51–64, 1994.
Barinaga, M. Science 1994. vol. 266 p. 1326.
Marshall, E. 1995 Science vol. 269, pp. 1050–1055.
Crystal, R. 1995 Science vol. 270 pp. 404–410.
Orkin, S.H. et al. 1995 Report and Recommendations of the Panel to Assess the NIH investment in Research on Gene Therapy. Dec. 1995. NIH Reports.
Bender, et al., *J. Virol.*, vol. 61, No. 5, pp. 1639–1646 (1987).
Miller, et al., *Biotechniques*, vol. 7, No. 9, pp. 980–990 (1989).
Wu et al. JBC. vol. 262, No. 10, pp. 4429–4432, Apr. 5, 1987.
Wu et al. JBC. vol. 232, No. 29, pp. 14621–14624, Oct. 1988.

*Primary Examiner*—Nancy Degen
*Assistant Examiner*—Irem Yucel
*Attorney, Agent, or Firm*—Elliot M. Olstein; Raymond J. Lillie

[57] ABSTRACT

A vector particle (e.g., a retroviral vector particle) containing a chimeric envelope includes a receptor binding region that binds to a receptor of a target cell. The receptor of the target cell is other than the amphotropic cell receptor. The receptor binding region may be a receptor binding region of a human virus. A portion of the envelope gene may be deleted and the deleted portion is replaced with another receptor binding region or ligand. Such vector particles are targetable to a desired target cell or tissue, and may be administered directly to the desired target cell or tissue as part of a gene therapy procedure, or administered directly into the patient.

28 Claims, 6 Drawing Sheets

TARGETABLE VECTOR PARTICLES

This application is a continuation of application Ser. No. 08/326,347, filed Oct. 20, 1994, abandoned, which is a continuation of application Ser. No. 07/973,307, filed Nov. 9, 1992, abandoned.

This invention relates to "targetable" vector particles. More particularly, this invention relates to vector particles which include a receptor binding region that binds to a receptor of a target cell of a human or non-human animal.

Vector particles are useful agents for introducing gene(s) or DNA (RNA) into a cell, such as a eukaryotic cell. The gene(s) is controlled by an appropriate promoter. Examples of vectors which may be employed to generate vector particles include prokaryotic vectors, such as bacterial vectors; eukaryotic vectors, including fungal vectors such as yeast vectors; and viral vectors such as DNA virus vectors, RNA virus vectors, and retroviral vectors. Retroviral vectors which have been employed for generating vector particles for introducing genes or DNA (RNA) into a cell include Moloney Murine Leukemia Virus, spleen necrosis virus, and vectors derived from retroviruses such as Rous Sarcoma Virus and Harvey Sarcoma Virus. The term "introducing" as used herein encompasses a variety of methods of transferring genes or DNA (RNA) into a cell, such methods including transformation, transduction, transfection, and infection.

Vector particles have been used for introducing DNA (RNA) into cells for gene therapy purposes. In general, such a procedure involves obtaining cells from a patient and using a vector particle to introduce desired DNA (RNA) into the cells and then providing the patient with the engineered cells for a therapeutic purpose. It would be desirable to provide alternative procedures for gene therapy. Such an alternative procedure would involve genetically engineering cells in vivo. In such a procedure, a vector particle which includes the desired DNA (RNA) would be administered directly to the target cells of a patient in vivo.

It is therefore an object of the present invention to provide gene therapy by introduction of a vector particle, such as, for example, a retroviral vector particle, directly into a desired target cell of a patient.

In accordance with an aspect of the present invention, there is provided a retroviral vector particle which includes a receptor binding region or ligand that binds to a receptor of a target cell. The receptor of the target cell is a receptor other than the amphotropic cell receptor.

Retroviruses have an envelope protein which contains a receptor binding region. Applicants have found that retroviruses can be made "targetable" to a specific type of cell if the receptor binding region of the retrovirus, which may be amphotropic, ecotropic, or xenotropic, among other types, is modified such that the receptor binding region of the envelope protein includes a receptor binding region which binds to a receptor of a target cell. For example, at least a portion of the receptor binding region of the envelope protein of the retrovirus is deleted and replaced with a receptor binding region or a ligand which binds to a receptor of a target cell. Thus, there is provided a retroviral vector wherein at least a portion of the DNA (RNA) which encodes the receptor binding region of the envelope protein of the retrovirus has been deleted and replaced with DNA (RNA) encoding a receptor binding region or a ligand which binds to a receptor of a target cell.

In one embodiment, the retrovirus is a murine leukemia virus.

The envelope of murine leukemia viruses includes a protein known as gp70. Such viruses can be made "targetable" to a specific type of cell if a portion of the gp70 protein is deleted and replaced with a receptor binding region or a ligand which binds to a receptor of a target cell. Thus, in a preferred embodiment, there is provided a retroviral vector wherein a portion, but not all, of the DNA (RNA) encoding gp70 protein has been deleted and replaced with DNA (RNA) encoding a receptor binding region or a ligand which binds to a receptor of a target cell.

In general, gp70 protein includes the following regions: (i) the secretory signal or "leader" sequence; (ii) the receptor binding domain; (iii) the hinge region; and (iv) the body portion. Preferably, at least a portion of the DNA (RNA) encoding the receptor binding domain of gp70 protein is deleted and replaced with DNA (RNA) encoding a receptor binding region or a ligand which binds to a receptor of a target cell. More preferably, DNA (RNA) encoding the entire receptor binding domain of gp70 protein is deleted and replaced with DNA (RNA) encoding a receptor binding region or a ligand which binds to a receptor of a target cell. In another embodiment, DNA (RNA) encoding the entire receptor binding domain of gp70 protein, plus all or a portion of the DNA (RNA) encoding the hinge region of gp70 protein is deleted and replaced with DNA (RNA) encoding a receptor binding region or a ligand of a target cell.

The gp70 protein may be derived from an ecotropic murine leukemia virus, a xenotropic murine leukemia virus, or an amphotropic murine leukemia virus. Ecotropic gp70 (or eco gp70) (SEQ ID NO:1) is a protein having 469 amino acids, and is encoded by (SEQ ID:2). Amino acid residues 1–33 constitute the leader sequence; amino acid residues 34–263 constitute the receptor binding domain; amino acid residues 264–312 constitute the hinge region; and amino acid residues 313–469 constitute the body portion. Preferably, DNA (RNA) encoding at least a portion of the receptor binding region is removed and replaced with DNA (RNA) encoding a receptor binding region or a ligand which binds to a receptor of a target cell. More preferably, DNA (RNA) encoding some or all of amino acid residues 34 to 263 (i.e., the receptor binding domain) is removed and replaced with DNA (RNA) encoding a receptor binding region or a ligand which binds to a receptor of a target cell.

Xenotropic gp70 (or xeno gp70) (SEQ ID NO:3) has 443 amino acid residues and is encoded by (SEQ ID NO:4). Amino acid residues 1–30 constitute the leader sequence; amino acid residues 31–232 constitute the receptor binding domain; amino acid residues 233–286 constitute the hinge region; and amino acid residues 287–443 constitute the body portion. Preferably, DNA (RNA) encoding at least a portion of the receptor binding region is removed and replaced with DNA (RNA) encoding a receptor binding region or a ligand which binds to a receptor of a target cell. More preferably, DNA (RNA) encoding some or all of amino acid residues 31 to 232 is removed and replaced with DNA (RNA) encoding a receptor binding region or a ligand which binds to a receptor of a target cell.

Target cells to which the retroviral vector particle may bind include, but are not limited to, liver cells, T-cells, lymphocytes, endothelial cells, T4 helper cells, and macrophages. In one embodiment, the retroviral vector particle binds to a liver cell, and in particular to hepatocytes. To enable such binding, the retroviral vector particle contains a chimeric protein encoded by DNA (RNA) in which at least a portion of the DNA (RNA) encoding the receptor binding domain of gp70 protein is removed and is replaced with DNA (RNA) which encodes a protein which binds to an asialoglycoprotein receptor (or ASG-R) of hepatocytes.

Proteins which bind to the asialoglycoprotein receptor of liver cells include, but are not limited to, asialoglycoproteins such as, for example, alpha-1-acid glycoprotein (AGP), also known as orosomucoid, and asialofetuin. AGP is a natural high-affinity ligand for ASG-R. The asialoglycoprotein receptor, or ASG-R, is expressed only by hepatocytes. The receptor is present at about $3 \times 10^5$ copies per cell, and such receptors have a high affinity for asialoglycoproteins such as AGP. Thus, the engineering of retroviral vector particles to contain asialoglycoprotein in place of the natural receptor binding domain of gp70 generates retroviral vector particles which bind to the asialoglycoprotein receptor of hepatocytes, which provides for an efficient means of transferring genes of interest to liver cells.

Cell lines which generate retroviral vector particles that are capable of targeting the hepatocyte's asialoglycoprotein receptor without the removal of the particle's terminal sialic acid groups by neuraminidase treatment, can be developed by selection with the cytotoxic lectin, wheat germ agglutinin (WGA). Cell lines which express the retroviral proteins gag and pol become retroviral vector packaging cell lines after they are transfected with the plasmids encoding chimeric envelope genes. These cell lines express the corresponding chimeric gp 70 glycoproteins. Upon exposure to successively higher concentrations of WGA, the outgrowth of cells which synthesize glycoproteins that lack terminal sialic acid groups, is favored. (Stanley, et al., *Somatic Cell Genetics, Vol.* 3, pgs. 391–405 (1977)). This selection permits the isolation of cells which synthesize oligosaccharides terminating in galactosyl sugar groups. Such cells will allow the construction of packaging cell lines that are capable of generating retroviral vector particles which target the asialoglycoprotein receptor. It is also possible to select subpopulations of packaging cells which have other distinct glycotypes, such cells yielding viral vectors that potentially are capable of targeting cells other than hepatocytes. Macrophages, for example, express unique, high-mannose receptors. The PHA-resistant subpopulation will have N-linked oligosaccharides which terminate in high-mannose groups (Stanley, et al., *In Vitro,* Vol. 12, pgs. 208–215 (1976)). Therefore, such a cell population will be capable of producing viral vector particles capable of targeting macrophoges via this receptor. Cells with mutant glycotypes which synthesize other novel oligosaccharides after selection with other cytotoxic lectins may also prove to be useful in targeting vector particles to other cell types such as lymphocytes or endothelial cells.

In another embodiment, the receptor binding region is a receptor binding region of a human virus. In one embodiment, the receptor binding region of a human virus is a hepatitis B virus surface protein binding region, and the target cell is a liver cell.

In another embodiment, the receptor binding region of a human virus is the gp46 protein of HTLV-I virus, and the target cell is a T-cell.

In yet another embodiment, the receptor binding region of a human virus is the HIV gp120 CD4 binding region, and the target cell is a T4 helper cell.

In one embodiment, the retroviral vector may be of the LN series of vectors, as described in Bender, et al., *J. Virol.,* Vol. 61, pgs. 1639–1649 (1987), and Miller, et al.; *Biotechniques,* Vol. 7, pgs. 98–990 (1989).

In another embodiment, the retroviral vector includes a multiple restriction enzyme site, or multiple cloning site. The multiple cloning site includes at least four cloning, or restriction enzyme sites, wherein at least two of the sites have an average frequency of appearance in eukaryotic genes of less than once in 10,000 base pairs; i.e., the restriction product has an average size of at least 10,000 base pairs.

In general, such restriction sites, also sometimes hereinafter referred to as "rare" sites, which have an average frequency of appearance in eukaryotic genes of leg than once in 10,000 base pairs, contain a CG doublet within their recognition sequence, such doublet appearing particularly infrequently in the mammalian genome. Another measure of rarity or scarcity of a restriction enzyme site in mammals is its representation in mammalian viruses, such as SV40. In general, an enzyme whose recognition sequence is absent in SV40 may be a candidate for being a "rare" mammalian cutter.

Examples of restriction enzyme sites having an average frequency of appearance in eukaryotic genes of less than once in 10,000 base pairs include, but are not limited to the NotI, SnaBI, SalI, XhoI, ClaI, SacI, EagI, and SmaI sites. Preferred cloning sites are selected from the group consisting of NotI, SnaBI, SalI, and XhoI.

Preferably, the multiple cloning site has a length no greater than about 70 base pairs, and preferably no greater than about 60 base pairs. In general, the multiple restriction enzyme site, or multiple cloning site is located between the 5' LTR and 3' LTR of the retroviral vector. The 5' end of the multiple cloning site is no greater than about 895 base pairs from the 3' end of the 5' LTR, preferably at least about 375 base pairs from the 3' end of the 5' LTR. The 3' end of the multiple cloning site is no greater than about 40 base pairs from the 5' end of the 3' LTR, and preferably at least 11 base pairs from the 5' end of the 3' LTR.

Such vectors may be engineered from existing retroviral vectors through genetic engineering techniques known in the art such that the retroviral vector includes at least four cloning sites wherein at least two of the cloning sites are selected from the group consisting of the NotI, SnaBI, SalI, and XhoI cloning sites. In a preferred embodiment, the retroviral vector includes each of the NotI, SnaBI, SalI, and XhoI cloning sites.

Such a retroviral vector may serve as part of a cloning system for the transfer of genes to such retroviral vector. Thus, there may be provided a cloning system for the manipulation of genes in a retroviral vector which includes a retroviral vector including a multiple cloning site of the type hereinabove described, and a shuttle cloning vector which includes at least two cloning sites which are compatible with at least two cloning sites selected from the group consisting of NotI, SnaBI, SalI, and XhoI located on the retroviral vector. The shuttle cloning vector also includes at least one desired gene which is capable of being transferred from said shuttle cloning vector to said retroviral vector.

The shuttle cloning vector may be constructed from a basic "backbone" vector or fragment to which are ligated one or more linkers which include cloning or restriction enzyme recognition sites. Included in the cloning sites are the compatible, or complementary cloning sites hereinabove described. Genes and/or promoters having ends corresponding to the restriction sites of the shuttle vector may be ligated into the shuttle vector through techniques known in the art.

The shuttle cloning vector may be employed to amplify DNA sequences in prokaryotic systems. The shuttle cloning vector may be prepared from plasmids generally used in prokaryotic systems and in particular in bacteria. Thus, for example, the shuttle cloning vector may be derived from plasmids such as pBR322; pUC18; etc.

Such retroviral vectors are transfected or transduced into a packaging cell line, whereby there are generated infectious vector particles which include the retroviral vector. In general, the vector is transfected into the packaging cell line along with a packaging defective helper virus which includes genes encoding the gag and pol, and the env proteins of the virus. Representative examples of packaging cell lines include, but are not limited to, the PE501 and PA317 cell lines disclosed in Miller, et al., *Biotechniques,* Vol. 7 pgs. 980–990 (1989).

The vector particles generated from the packaging cell line, which are also engineered with a protein containing a receptor binding region that binds to a receptor of a target cell, said receptor being other than the amphotropic cell receptor, are targetable, whereby the receptor binding region enables the vector particles to bind to a target cell. The retroviral vector particles thus may be directly administered to a desired target cell ex vivo, and such cells may then be administered to a patient as part of a gene therapy procedure.

Although the vector particles may be administered directly to a target cell, the vector particles may be engineered such that the vector particles are "injectable" as well as targetable; i.e., the vector particles are resistant to inactivation by human serum, and thus the targetable vector particles may be administered to a patient by intravenous injection, and travel directly to a desired target cell or tissue without being inactivated by human serum.

The envelope of retroviruses also includes a protein known as p15E, and Applicants have found that retroviruses are susceptible to inactivation by human serum a a result of the action of complement protein(s) present in serum on the p15E protein portion of the retrovirus. Applicants have further found that such retroviruses can be made resistant to inactivation by human serum by mutating such p15E protein.

In one embodiment, therefore, the retroviral vector is engineered such that a portion of the DNA (RNA) encoding p15E protein (shown in the accompanying sequence listing as SEQ ID NO:7), has been mutated to render the vector particle resistant to inactivation by human serum; i.e., at least one amino acid but not all of the amino acids of the p15E protein has been changed, or mutated.

p15E protein is a viral protein having 196 amino acid residues. In viruses, sometimes all 196 amino acid residues are present, and in other viruses, amino acid residues 181 to 196 (known as the "r" peptide), are not present, and the resulting protein is the "mature" form of p15E known as p12E. Thus, viruses can contain both the p15E and p12E proteins. p15E protein is anchored in the viral membrane such that amino acid residues residues 1 to 134 are present on the outside of the virus. Although this embodiment of the present invention is not to be limited to any of the following reasoning, Applicants believe complement proteins may bind to this region whereby such binding leads to inactivation and/or lysis of the retrovirus. In particular, the p15E protein includes two regions, amino acid residues 39 to 61 (sometimes hereinafter referred to as region 1), and amino acid residues 101 to 123 (sometimes hereinafter referred to as region 2), which Applicants believe have an external location in the three-dimensional structure of the p15E protein; i.e., such regions are directly exposed to human serum. Region 2 is a highly conserved region in many retroviruses, even though the amino acid sequences of this region are not identical in all retroviruses. Such regions are complement binding regions. Examples of complement proteins which may bind to the complement binding regions are ClS and ClQ, which bind to regions 1 and 2.

In order to inactivate the retrovirus, complement proteins bind to both region 1 and region 2. Thus, in a preferred embodiment, at least one portion of DNA encoding a complement binding region of p15E protein has been mutated. Such a mutation results in a change of at least one amino acid residue of a complement binding region of p15E protein. The change in at least one amino acid residue of a complement binding region of p15E protein prevents binding of a complement protein to the complement binding region, thereby preventing complement inactivation of the retrovirus. In one embodiment, at least one amino acid residue in both complement binding regions of p15E protein is changed, whereas in another embodiment, at least one amino acid residue in one of the complement binding regions is changed.

It is to be understood, however, that the entire DNA sequence encoding p15E protein cannot be mutated because such a change renders the vectors unsuitable for in vivo use.

In one embodiment, the mutation of DNA (RNA) encoding p15E protein may be effected by deleting a portion of the p15E gene, and replacing the deleted portion of the p15E gene, with fragment(s) or portion(s) of a gene encoding another viral protein. In one embodiment, one portion of DNA encoding the p15E protein is replaced with a fragment of the gene encoding the p21 protein, which is an HTLV-I transmembrane protein. HTLV-I virus has been found to be resistant to binding by complement proteins and thus HTLV-I is resistant to inactivation by human serum (Hoshino, et al., *Nature,* Vol. 310, pgs. 324–325 (1984)). Thus, in one embodiment, there is also provided a retroviral vector particle wherein a portion of the p15E protein has been deleted and replaced with a portion of another viral protein, such as a portion of the p21 protein.

p21 protein (as shown in the accompanying sequence listing as SEQ ID NO:8) is a protein having 176 amino acid residues, and which, in relation to p15E, has significant amino acid sequence homology. In one embodiment, at least amino acid residues 39 to 61, and 101 to 123 are deleted from p15E protein, and replaced with amino acid residues 34 to 56 and 96 to 118 of p21 protein.

In one alternative, at least amino acid residues 39 to 123 of p15E protein are deleted and replaced with amino acid residues 34 to 118 of p21 protein.

In another embodiment, amino acid residues 39 to 69 of p15E protein are deleted and replaced with amino acid residues 34 to 64 of p21 protein, and amino acid residues 96 to 123 of p15E protein are deleted and replaced with amino acid residues 91 to 118 of p21 protein.

Vector particles generated from such packaging lines, therefore, are "targetable" and "injectable," whereby such vector particles, upon administration to a patient, travel directly to a desired target cell or tissue.

The targetable vector particles are useful for the introduction of desired heterologous genes into target cells ex vivo. Such cells may then be administered to a patient as a gene therapy procedure, whereas vector particles which are targetable and injectable may be administered in vivo to the patient, whereby the vector particles travel directly to a desired target cell.

Thus, preferably, the vectors or vector particles of the present invention further include at least one heterologous gene. Heterologous or foreign genes which may be placed into the vector or vector particles include, but are not limited to, genes which encode cytokines or cellular growth factors, such as lymphokines, which are growth factors for lymphocytes. Other examples of foreign genes include, but are not limited to, genes encoding Factor VIII, Factor IX, tumor necrosis factors (TNF's), ADA, ApoE, ApoC, and Protein C.

The vectors of the present invention include one or more promoters. Suitable promoters which may be employed include, but are not limited to, the retroviral LTR; the SV40 promoter; and the human cytomegalovirus (CMV) promoter described in Miller, et al., *Biotechniques,* Vol. 7, No. 9, pgs 980–990 (1989), or any other promoter (e.g., cellular promoters such as eukaryotic cellular promoters including, but not limited to, the histone, pol III, and B-actin promoters). Other viral promoters which may be employed include, but are not limited to, adenovirus promoters, TK promoters, and B19 parvovirus promoters. The selection of a suitable promoter will be apparent to those skilled in the art from the teachings contained herein.

The vectors of the present invention may contain regulatory elements, where necessary to ensure tissue specific expression of the desired heterologous gene(s), and/or to regulate expression of the heterologous gene(s) in response to cellular or metabolic signals.

Although the invention has been described with respect to retroviral vector particles, other viral vector particles (such as, for example, adenovirus, adeno-associated virus, and Herpes Simplex virus particles), or synthetic particles may be constructed such that the vector particles include a receptor binding region that binds to a receptor of a target cell, wherein the receptor of a human target cell is other than the amphotropic cell receptor. Such vector particles are suitable for in vivo administration to a desired target cell.

Advantages of the present invention include the ability to provide vector particles which may be administered directly to a desired target cell or tissues, whereby desired genes are delivered to the target cell or tissue, whereby the target cell or tissue may produce the proteins expressed by such genes.

BRIEF DESCRIPTION OF THE DRAWINGS

The invention now will be described with respect to the drawings, wherein.

This invention will now be described with respect to the following examples; however, the scope of the present invention is not intended to be limited thereby.

EXAMPLE 1

Figure 1:
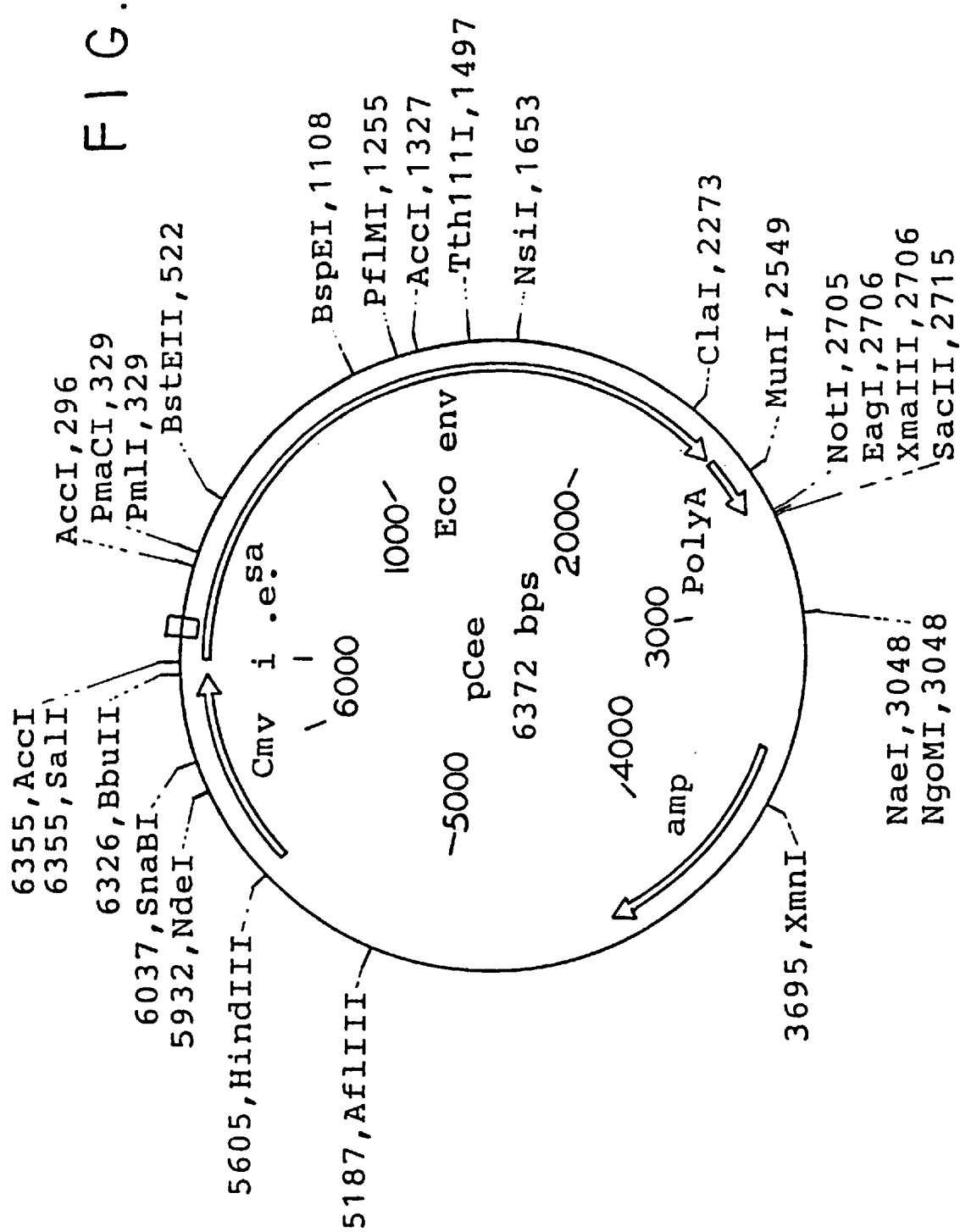
FIG. 1 is a nap of plasmid pCEE.
Figure 2:
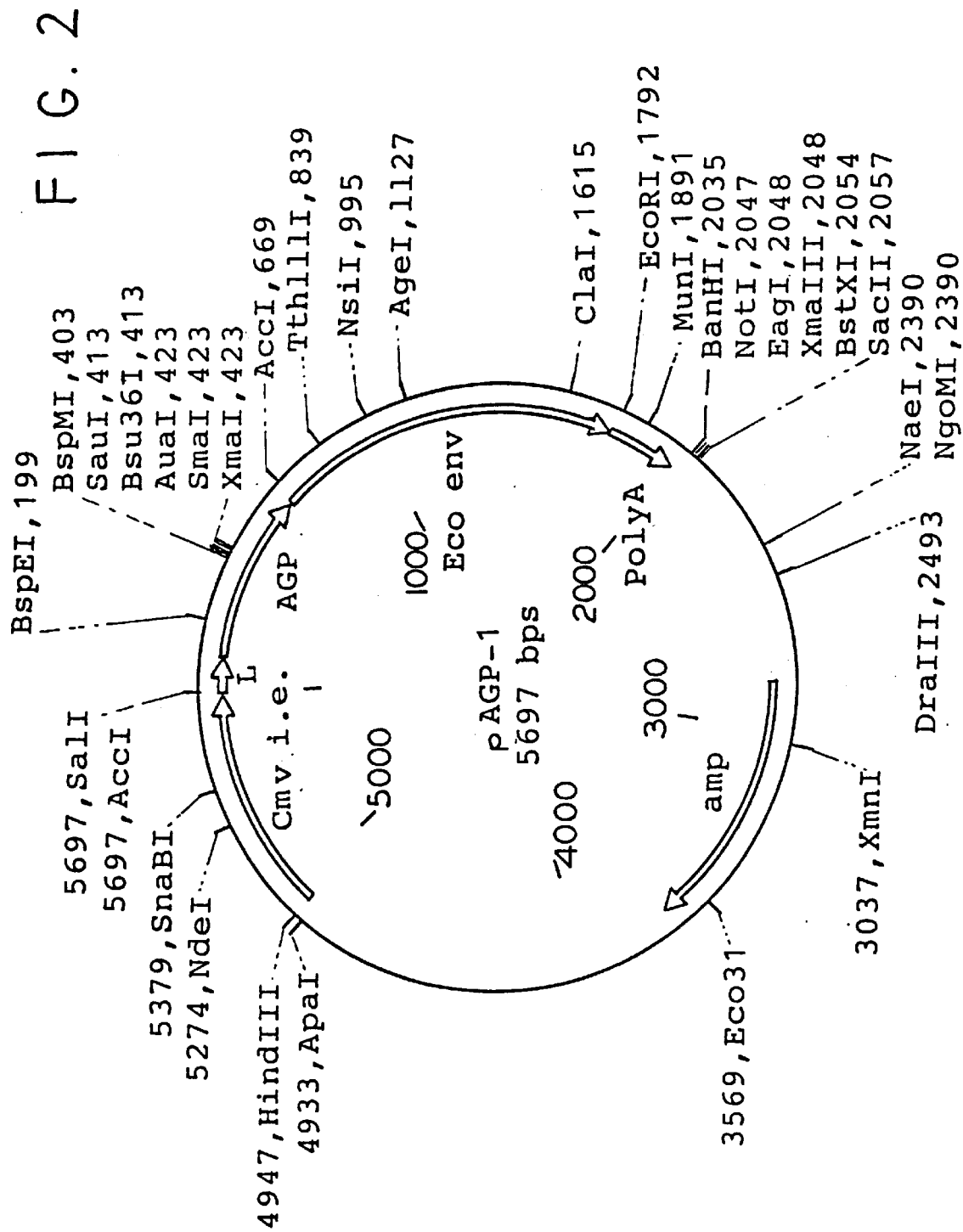
FIG. 2 is a map of plasmid pAGP-1.

Plasmid pCee (FIG. 1), which contains the ecotropic murine leukemia virus gp70 and p15E genes under the control of a CMV promoter, was cut with AccI, and an AccI fragment encoding amino acid residues 1–312 of the eco gp70 protein was removed. Cloned into the AccI site was a PCR fragment containing the eco gp70 secretion signal (or leader, which includes amino acid residues 1–33 of eco gp70), followed by mature rabbit alpha-1 acid glycoprotein (amino acid residues 19–201) (Ray, et al., *Biochemical and Biophysical Research Communications,* Vol. 178, No. 2, pgs. 507–513 (1991)). The amino acid sequence of rabbit alpha-1 acid glycoprotein is shown in (SEQ ID NO:5), and the DNA sequence encoding therefor is shown in (SEQ ID NO:6). The resulting plasmid pAGP-1 (FIG. 2) contains the eco gp70 leader sequence (amino acid residues 1–33 of eco gp70), a sequence encoding the mature rabbit alpha-1 acid glycoprotein (amino acid residues 19–201), and a sequence encoding amino acid residues 313 to 469 of eco gp70.

EXAMPLE 2

Figure 3:
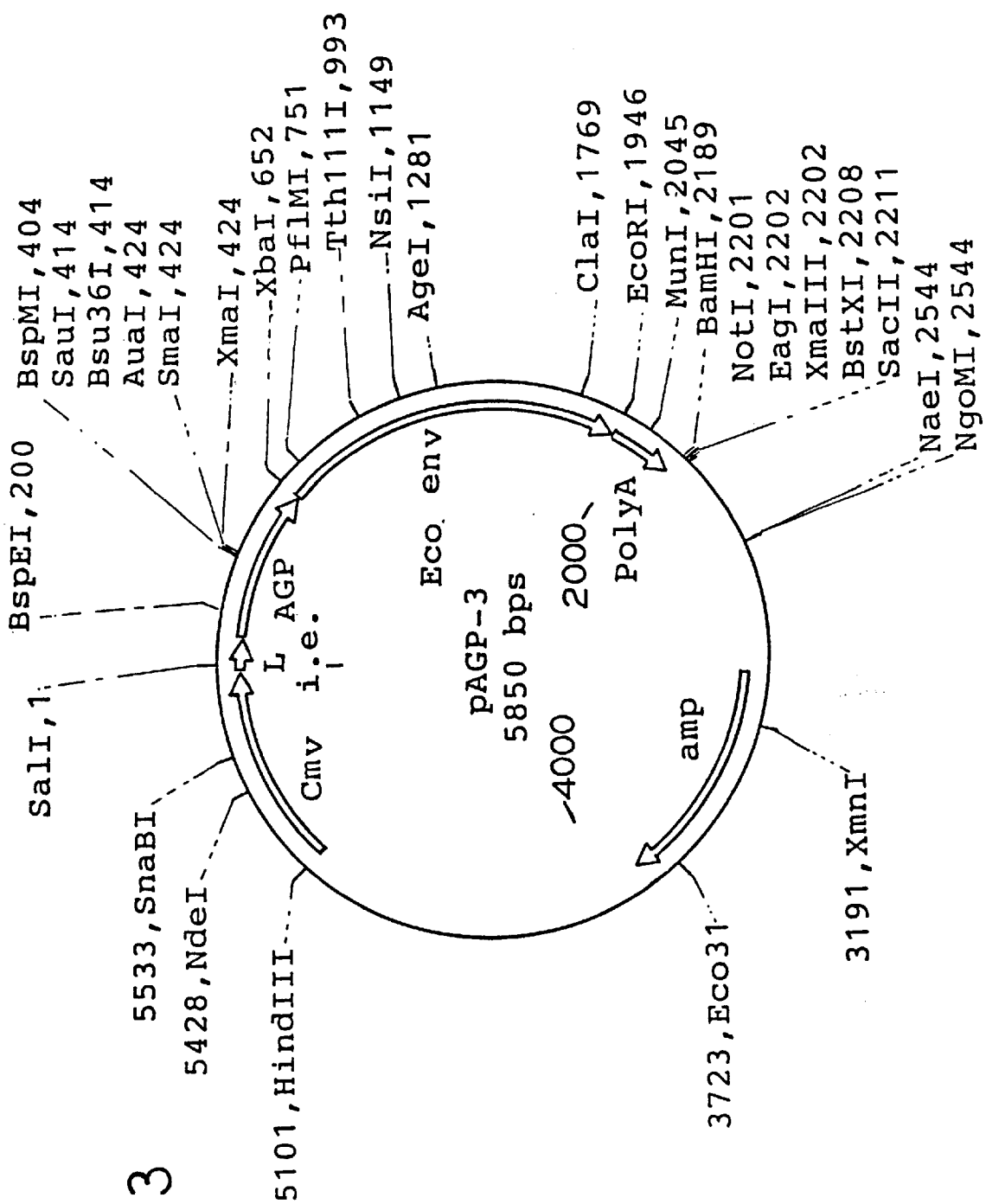
FIG. 3 is a map of plasmid pAGP-3.

Plasmid pCee was cut with SalI and Pf1MI, and a SalI-Pf1MI fragment encoding amino acid residues 1–262 of eco gp70 was removed. Cloned into this site was a PCR generated SalI-Pf1MI fragment containing the eco gp70 leader sequence and the sequence encoding mature rabbit alpha-1 acid glycoprotein. The resulting plasmid, pAGP-3 (FIG. 3) thus includes a sequence encoding the leader sequence of eco gp70, a sequence encoding mature rabbit alpha-1 acid glycoprotein; and a sequence encoding amino acid residues 263 to 469 of eco gp70.

EXAMPLE 3

Figure 4:
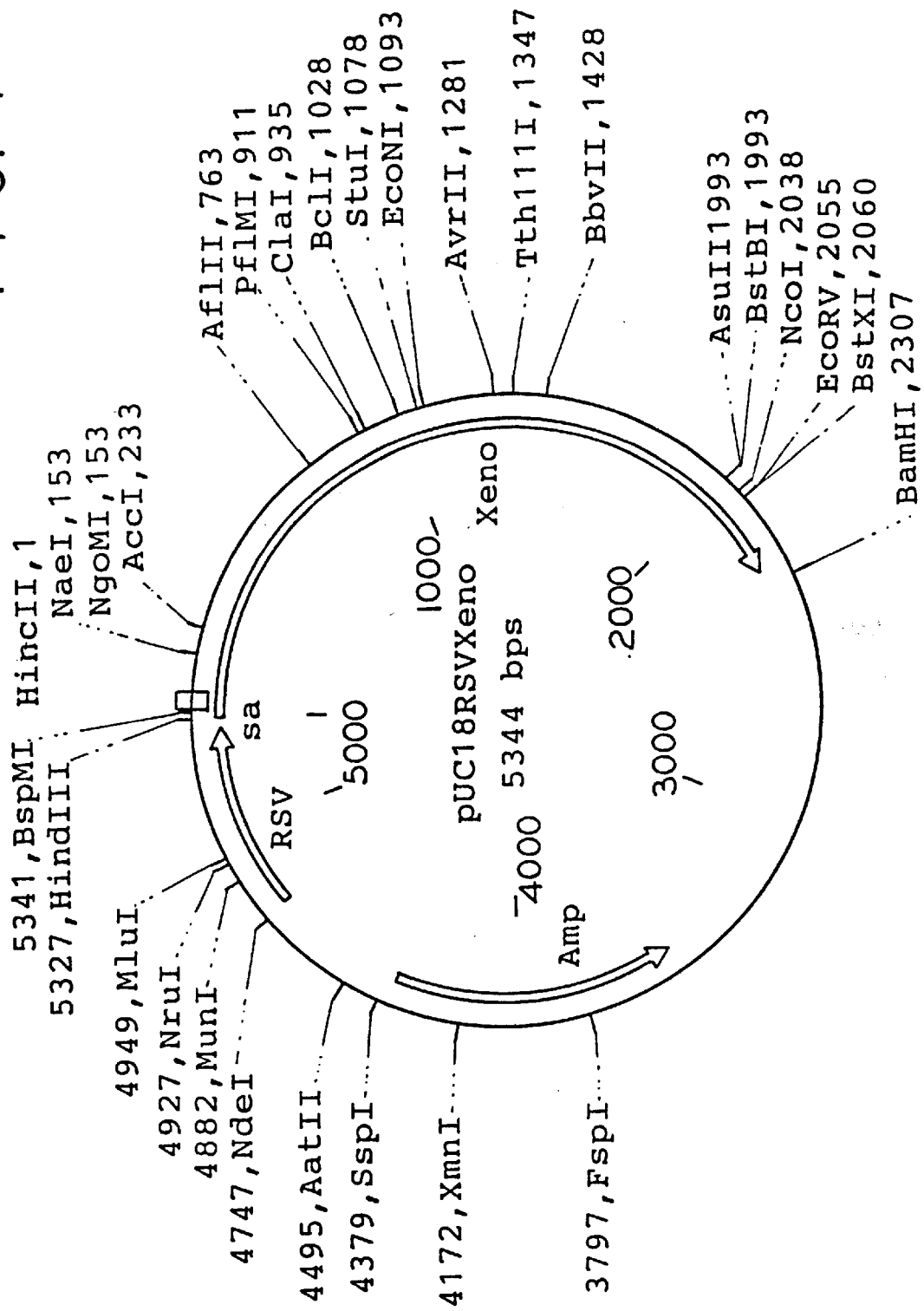
FIG. 4 is a map of plasmid pUCI 8RSVXeno.
Figure 5:
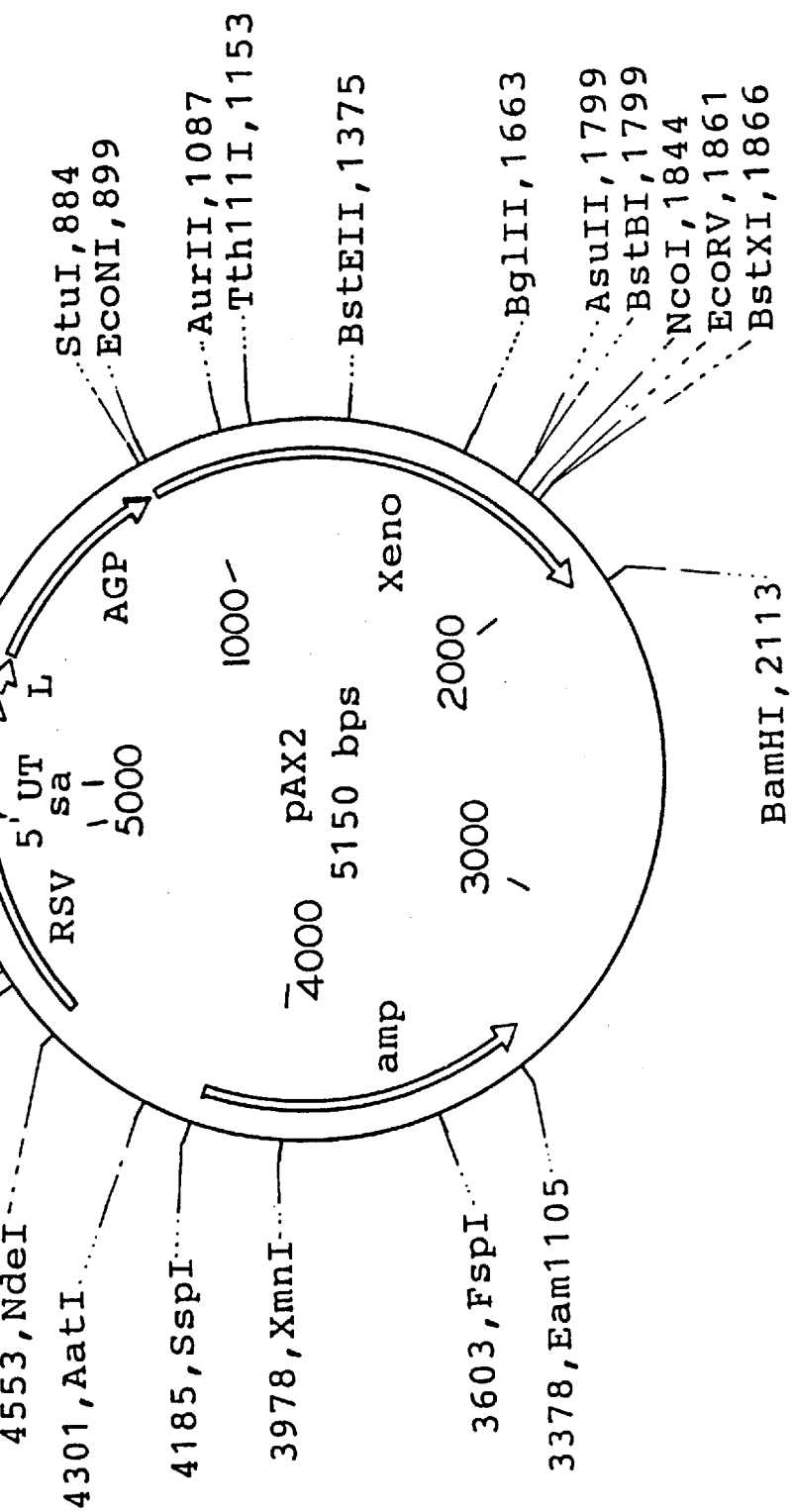
FIG. 5 is a map of plasmid pAX2.

Plasmid pUC18RSVXeno (FIG. 4), which contains the xenotrophic murine leukemia virus gp70 and p15E genes under the control of an RSV promoter, was cut with AccI and StuI, and an AccI-StuI fragment encoding amino acid residues 1–258 of xeno gp70 was removed. Cloned into this site was a PCR generated AccI-StuI fragment encoding the xeno gp70 leader (amino acid residues 1–30), and the mature rabbit alpha-1 acid glycoprotein. The resulting plasmid, pAX2 (FIG. 5), thus contains a sequence encoding the xeno gp70 leader, a sequence encoding the mature rabbit alpha-I acid glycoprotein, and amino acid residues 259–443 of xeno gp70.

EXAMPLE 4

Figure 6:
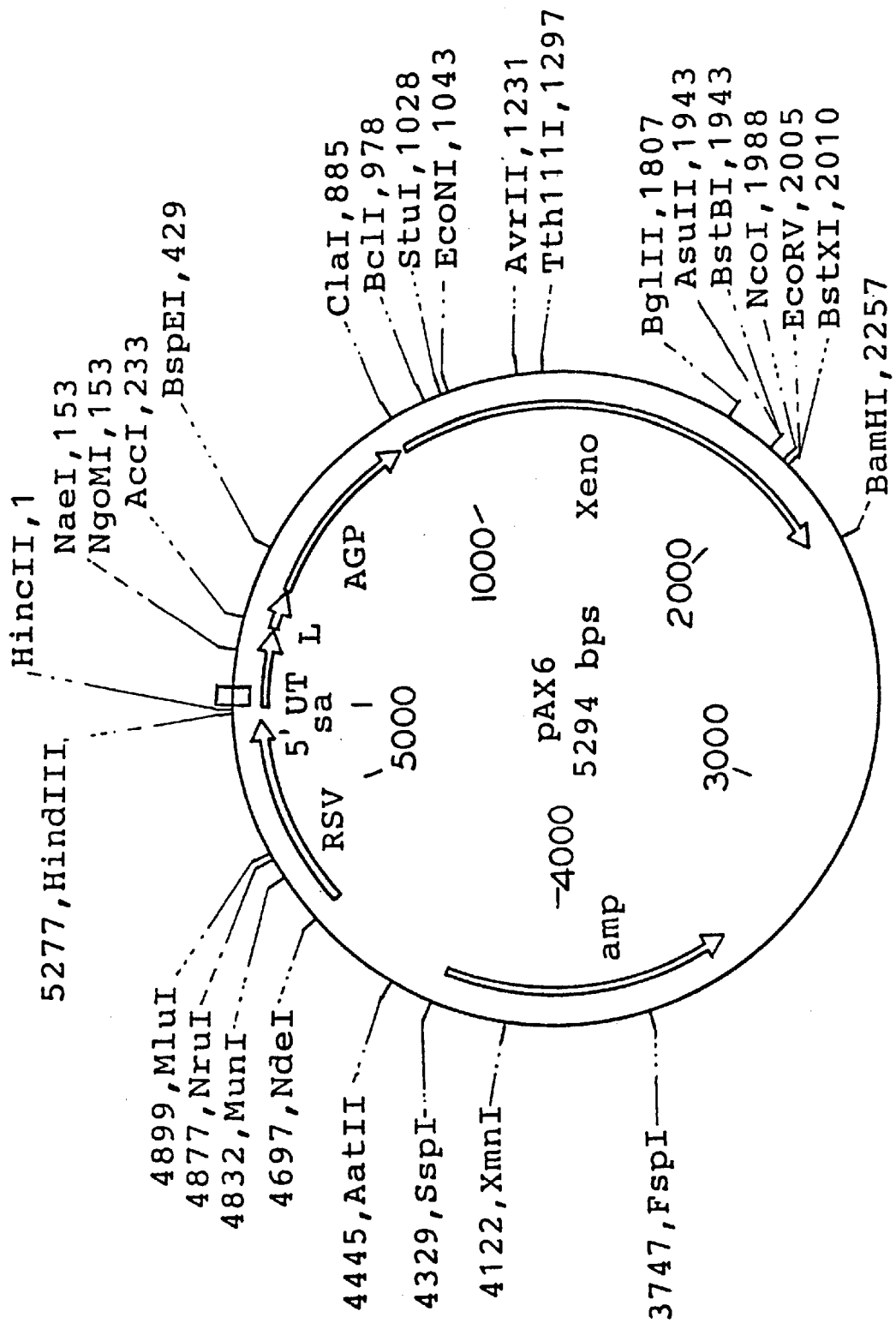
FIG. 6 is a map of plasmid pAX6.

Plasmid pUC18RSVXeno was cut with AccI and ClaI, and a fragment encoding amino acid residues 1–210 of xeno gp70 was removed. Cloned into this site was a PCR generated AccI-ClaI fragment encoding the xeno gp70 leader, followed by mature rabbit alpha-1 acid glycoprotein. The resulting plasmid, pAX6 (FIG. 6), thus includes a sequence encoding the xeno gp70 leader, a sequence encoding mature rabbit alpha-1 acid giycoprotein, and amino acid residues 211–443 of xeno gp70.

EXAMPLE 5

$5 \times 10^5$ GPL cells on 10 cm tissue culture plates were transfected (using $CaPO_4$) with 30 µg/plate of one of plasmids pAGP-1, pAGP-3, pAX2, or pAX6. The $CaPO_4$ is removed 24 hours later and 10 ml of fresh D1O medium is added for another 24 hours. The D10 medium is then removed and replaced with serum free DX medium for another 24 hours. The DX medium is then collected, filtered, and stored on ice. This supernatant contains the vector particles.

The supernatants were then filtered and collected by standard procedures and then centrifuged. After centrifugation, the virus pellets were reconstituted in a buffer containing 0.1M sodium acetate, 0.15M sodium chloride, and 2 mM calcium chloride; the buffer was sterilized using a Falcon 0.2 millimicron tissue culture filter.

2.2 ml of concentrated supernatant containing viral particles generated from pAGP-1 or pAGP-3, said viral particles sometimes hereinafter referred to as Chimeric-1 or Chimeric-3, were loaded onto two disposable plastic columns which were alcohol sterilized and dried. To each column (1 cm×6 cm), one unit of neuraminidase from *Clostridium perfringens* which was bound to beaded agarose was added as a 2 ml suspension. This represents 1 ml of packed gel or unit of enzyme per column (15.7 mg of agarose/ml and 28 units per gram of agarose). A unit is defined as the amount of neuraminidase which will liberate 1.0 micromole of N-acetylneuraminic acid per minute from NAN-lactose at pH 5.0 and 37° C.

The columns were then washed with a large excess (50 ml) of the buffer hereinabove described to free the resin of all traces of free neuraminidase and to sterilize the resin prior to incubation with virus. The columns were then dried, and the bottoms were sealed with caps and secured with parafilm. The concentrated virus which was reconstituted in the buffer (2.0 ml per sample) was then added to the resin. The tops were placed on the columns and secured with parafilm. The resin was gently re-suspended by hand The virus was then incubated with the resin for 1 hour at room temperature with gentle rotation on a wheel. The columns were checked periodically to ensure good mixing of resin and virus.

At the end of the incubation period, the Chimera-1 and Chimera-3 viruses were recovered by gentle vacuum filtration and collected into separate sterile 12×75 mm plastic polypropylene Falcon 2063 tubes. Recovery was greater than 90%, giving about 1.8 ml of desialated virus.

6-well plates containing about $10^5$ receptor-positive (Hep G2) or receptor-negative (SK HepI) human hepatocytes in 2 ml D10 media were employed as target cells. 24 hours after the cells were plated, 1 ml of D10 was removed from the first well and 2 ml of neuraminidase-treated (or untreated as a control) viral supernatant containing Chimeric-1 or Chimeric-3 was added and mixed well. 200 ul from the first well was diluted into the 2 ml present in the second well, was then mixed; and then 200 ul from the second well was diluted into the 1.8 ml present in the third well, thereby giving approximate dilutions of 2/3, 1/15, and 1/150. 8 ug/ml of Polybrene was included in each well during the transduction. The viral particles were left in contact with the cells overnight, followed by removal of media containing viral particles, and replaced with D10 containing 1,000 mg/ml of G418. The medium was changed with fresh D10 and G418 every 4 to 5 days as necessary. G418-resistant colonies were scored after 2 to 3 weeks.

EXAMPLE 6

The pre-packaging cell line GP8, which expresses the retroviral proteins gag and pol, and the packaging cell lines derived from them which also express the chimeric gp70 glycoproteins encoded by the plasmids pAGP-1, pAGP-3, pAX2, or pAX6 were maintained in cell culture and exposed to successively higher concentrations of wheat germ agglutinin; starting with 15 ug/ml. The cell lines were maintained under WGA selection in cell culture for 6 to 8 weeks until populations resistant to 40–50 ug/ml WGA were obtained. The latter were then subjected to fluoresence-activated cell sorting using FITC-conjugated lectins to enrich for the cells expressing the desired mutant glycotype (e.g., FITC-*Erythrina Cristagalli* agglutinin for beta-D-galactosyl groups, and FITC-concanavalin A for alpha-D-mannosyl groups). Retroviral vector packaging and producer cell lines were then generated from the resulting populations by standard techniques.

It is to be understood, however, that the scope of the present invention is not to be limited to the specific embodiments described above. The invention may be practiced other than as particularly described and still be within the scope of the accompanying claims.

What is claimed is:

1. A retroviral vector particle, said retroviral vector particle including a retroviral envelope protein, which includes a receptor binding region, a hinge region, and a body region, wherein a portion of said retroviral envelope protein is deleted and a receptor binding region or a ligand that binds to a receptor of a target cell is inserted into said deleted portion, said receptor of a target cell being other than the amphotropic cell receptor, and wherein the only portion of the retroviral envelope protein that is deleted is (i) a portion or all of the receptor binding region, (ii) a portion of the receptor binding region and a portion or all of the hinge region, or (iii) all of the receptor binding region and a portion or all of the hinge region.

2. The retroviral vector particle of claim 1 wherein a portion of the receptor binding region of said retroviral envelope protein is deleted.

3. The retroviral vector particle of claim 1 wherein all of the receptor binding region of the retroviral envelope protein is deleted.

4. The retroviral vector particle of claim 1 wherein all of the receptor binding region and a portion of the hinge region of the retroviral envelope protein are deleted.

5. The retroviral vector particle of claim 1 wherein said receptor binding region that binds to a receptor of a target cell is a receptor binding region of a human virus.

6. The retroviral vector particle of claim 5 wherein said receptor binding region of a human virus is a hepatitis B virus surface protein binding region and said target cell is a liver cell.

7. The retroviral vector particle of claim 5 wherein said receptor binding region of a human virus is the receptor binding region of gp46 of HTLV-I virus and said target cell is a T-cell.

8. The retroviral vector particle of claim 5 wherein said receptor binding region of a human virus is the HIV gp 120 CD4 binding region and said target cell is a T4 helper cell.

9. The retroviral vector particle of claim 1 wherein said receptor binding region or ligand that binds to a receptor of a target cell, which is inserted into said deleted portion is a protein which binds to an asialoglycoprotein receptor of hepatocytes.

10. The retroviral vector particle of claim 9 wherein said protein which binds to an asialoglycoprotein receptor of hepatocytes is alpha-1 acid glycoprotein.

11. The retroviral vector particle of claim 1 further including at least one heterologous gene.

12. A packaging cell line which produces the retroviral vector particles of claim 1.

13. The retroviral vector particle of claim 1 wherein said vector particle is a Moloney Murine Leukemia Virus particle.

14. The retroviral vector particle of claim 13 wherein a portion of the receptor binding region of said retroviral envelope protein is deleted.

15. The retroviral vector particle of claim 13 wherein all of the receptor binding region of the retroviral envelope protein is deleted.

16. The retroviral vector particle of claim 13 wherein all of the receptor binding region and a portion of the hinge region of the retroviral envelope protein are deleted.

17. The retroviral vector particle of claim 13 wherein said receptor binding region that binds to a receptor of a target cell is a receptor binding region of a human virus.

18. The retroviral vector particle of claim 17 wherein said receptor binding region of a human virus is a hepatitis B virus surface protein binding region and said target cell is a liver cell.

19. The retroviral vector particle of claim 17 wherein said receptor binding region of a human virus is the receptor binding region of gp46 of HTLV-I virus and said target cell is a T-cell.

20. The retroviral vector particle of claim 17 wherein said receptor binding region of a human virus is the HIV gp 120 CD4 binding region and said target cell is a T4 helper cell.

21. The retroviral vector particle of claim 19 wherein said receptor binding region or ligand that binds to a receptor of a target cell, which is inserted into said deleted portion is a protein which binds to an asialoglycoprotein receptor of hepatocytes.

22. The retroviral vector particle of claim 21 wherein said protein which binds to an asialoglycoprotein receptor of hepatocytes is alpha-1 acid glycoprotein.

23. The retroviral vector particle of claim 13 further including at least one heterologous gene.

24. The retroviral vector particle of claim 13 wherein said retroviral envelope protein is an ecotropic envelope including a gp70 protein having the sequence (SEQ ID NO:1), and wherein amino acid residues 34 through 312 of (SEQ ID NO:1) are deleted.

25. The retroviral vector particle of claim 13 wherein said retroviral envelope protein is an ecotropic envelope including a gp70 protein having the sequence (SEQ ID NO:1), and wherein amino acid residues 34 through 262 of (SEQ ID NO:1) are deleted.

26. The retroviral vector particle of claim 13 wherein said retroviral envelope protein is a xenotropic envelope including a gp70 protein having the sequence (SEQ ID NO:3), and wherein amino acid residues 31 through 258 of (SEQ ID NO:3) are deleted.

27. The retroviral vector particle of claim 13 wherein said retroviral envelope protein is a xenotropic envelope including a gp70 protein having the sequence (SEQ ID NO:3), and wherein amino acid residues 31 through 210 of (SEQ ID NO:3) are deleted.

28. A packaging cell line which produces the retroviral vector particles of claim 13.

* * * * *

```
                         SEQUENCE LISTING (1) GENERAL INFORMATION:

(iii) NUMBER OF SEQUENCES:  8

(2) INFORMATION FOR SEQ ID NO: 1:

(i) SEQUENCE CHARACTERISTICS:
          (A) LENGTH: 469 amino acids
          (B) TYPE:     amino acid
          (C) STRANDEDNESS:
          (D) TOPOLOGY: linear (ii) MOLECULE TYPE:  protein (ix) FEATURE:
          (A) NAME/KEY:  Ecotropic gp70 Protein (xi) SEQUENCE DESCRIPTION: SEQ ID NO:1:

Met Ala Arg Ser Thr Leu Ser Lys Pro Leu
                5                   10

Lys Asn Lys Val Asn Pro Arg Gly Pro Leu
                15                  20

Ile Pro Leu Ile Leu Leu Met Leu Arg Gly
                25                  30

Val Ser Thr Ala Ser Pro Gly Ser Ser Pro
                35                  40

His Gly Val Tyr Asn Ile Thr Trp Glu Val
                45                  50

Thr Asn Gly Asp Arg Glu Thr Val Trp Ala
                55                  60

Thr Ser Gly Asn His Pro Leu Trp Thr Trp
```

```
                        65                  70
Trp Pro Asp Leu Thr Pro Asp Leu Cys Met
                    75                  80
Leu Ala His His Gly Pro Ser Tyr Trp Gly
                    85                  90
Leu Glu Tyr Gln Ser Pro Phe Ser Ser Pro
                    95                  100
Pro Gly Pro Pro Cys Cys Ser Gly Gly Ser
                    105                 110
Ser Pro Gly Cys Ser Arg Asp Cys Glu Glu
                    115                 120
Pro Leu Thr Ser Leu Thr Pro Arg Cys Asn
                    125                 130
Thr Ala Trp Asn Arg Leu Lys Leu Asp Gln
                    135                 140
Thr Thr His Lys Ser Asn Glu Gly Phe Tyr
                    145                 150
Val Cys Pro Gly Pro His Arg Pro Arg Glu
                    155                 160
Ser Lys Ser Cys Gly Gly Pro Asp Ser Phe
                    165                 170
Tyr Cys Ala Tyr Trp Gly Cys Glu Thr Thr
                    175                 180
Gly Arg Ala Tyr Trp Lys Pro Ser Ser Ser
                    185                 190
Trp Asp Phe Ile Thr Val Asn Asn Asn Leu
                    195                 200
Thr Ser Asp Gln Ala Val Gln Val Cys Lys
                    205                 210
Asp Asn Lys Trp Cys Asn Pro Leu Val Ile
                    215                 220
Arg Phe Thr Asp Ala Gly Arg Arg Val Thr
                    225                 230
Ser Trp Thr Thr Gly His Tyr Trp Gly Leu
                    235                 240
Arg Leu Tyr Val Ser Gly Gln Asp Pro Gly
                    245                 250
Leu Thr Phe Gly Ile Arg Leu Arg Tyr Gln
                    255                 260
Asn Leu Gly Pro Arg Val Pro Ile Gly Pro
                    265                 270
Asn Pro Val Leu Ala Asp Gln Gln Pro Leu
                    275                 280
Ser Lys Pro Lys Pro Val Lys Ser Pro Ser
                    285                 290
Val Thr Lys Pro Pro Ser Gly Thr Pro Leu
                    295                 300
Ser Pro Thr Gln Leu Pro Pro Ala Gly Thr
                    305                 310
Glu Asn Arg Leu Leu Asn Leu Val Asp Gly
                    315                 320
Ala Tyr Gln Ala Leu Asn Leu Thr Ser Pro
                    325                 330
```

Asp Lys Thr Gln Glu Cys Trp Leu Cys Leu
            335                 340

Val Ala Gly Pro Pro Tyr Tyr Glu Gly Val
            345                 350

Ala Val Leu Gly Thr Tyr Ser Asn His Thr
            355                 360

Ser Ala Pro Ala Asn Cys Ser Val Ala Ser
            365                 370

Gln His Lys Leu Thr Leu Ser Glu Val Thr
            375                 380

Gly Gln Gly Leu Cys Ile Gly Ala Val Pro
            385                 390

Lys Thr His Gln Ala Leu Cys Asn Thr Thr
            395                 400

Gln Thr Ser Ser Arg Gly Ser Tyr Tyr Leu
            405                 410

Val Ala Pro Thr Gly Thr Met Trp Ala Cys
            415                 420

Ser Thr Gly Leu Thr Pro Cys Ile Ser Thr
            425                 430

Thr Ile Leu Asn Leu Thr Thr Asp Tyr Cys
            435                 440

Val Leu Val Glu Leu Trp Pro Arg Val Thr
            445                 450

Tyr His Ser Pro Ser Tyr Val Tyr Gly Leu
            455                 460

Phe Glu Arg Ser Asn Arg His Lys Arg
            465

(2) INFORMATION FOR SEQ ID NO: 2:

(i) SEQUENCE CHARACTERISTICS:
       (A) LENGTH: 1446 bases
       (B) TYPE: nucleic acid
       (C) STRANDEDNESS: single
       (D) TOPOLOGY: linear (ii) MOLECULE TYPE: viral DNA (xi) SEQUENCE DESCRIPTION: SEQ ID NO:2:

```
GGCTGCCGAC CCCGGGGGTG GACCATCCTC TAGACTGACA TGGCGCGTTA AACGCTCTCA      60

AAACCCCTTA AAAATAAGGT TAACCCGCGA GGCCCCCTAA TCCCCTTAAT TCTTCTGATG     120

CTCAGAGGGG TCAGTACTGC TTCGCCCGGC TCCAGTCCTC ATCAAGTCTA TAATATCACC     180

TGGGAGGTAA CCAATGGAGA TCGGGAGACG GTATGGGCAA CTTCTGGCAA CCACCCTCTG     240

TGGACCTGGT GGCCTGACCT TACCCCAGAT TTATGTATGT TAGCCCACCA TGGACCATCT     300

TATTGGGGGC TAGAATATCA ATCCCCTTTT TCTTCTCCCC CGGGGCCCCC TTGTTGCTCA     360

GGGGGCAGCA GCCCAGGCTG TTCCAGAGAC TGCGAAGAAC CTTTAACCTC CCTCACCCCT     420

CGGTGCAACA CTGCCTGGAA CAGACTCAAG CTAGACCAGA CAACTCATAA ATCAAATGAG     480

GGATTTTATG TTTGCCCCGG GCCCCACCGC CCCCGAGAAT CCAAGTCATG TGGGGGTCCA     540

GACTCCTTCT ACTGTGCCTA TTGGGGCTGT GAGACAACCG GTAGAGCTTA CTGGAAGCCC     600

TCCTCATCAT GGGATTTCAT CACAGTAAAC AACAATCTCA CCTCTGACCA GGCTGTCCAG     660

GTATGCAAAG ATAATAAGTG GTGCAACCCC TTAGTTATTC GGTTTACAGA CGCCGGGAGA     720
```

```
CGGGTTACTT CCTGGACCAC AGGACATTAC TGGGGCTTAC GTTTGTATGT CTCCGGACAA      780

GATCCAGGGC TTACATTTGG GATCCGACTC AGATACCAAA ATCTAGGACC CCGCGTCCCA      840

ATAGGGCCAA ACCCCGTTCT GGCAGACCAA CAGCCACTCT CCAAGCCCAA ACCTGTTAAG      900

TCGCCTTCAG TCACCAAACC ACCCAGTGGG ACTCCTCTCT CCCCTACCCA ACTTCCACCG      960

GCGGGAACGG AAAATAGGCT GCTAAACTTA GTAGACGGAG CCTACCAAGC CCTCAACCTC     1020

ACCAGTCCTG ACAAAACCCA AGAGTGCTGG TTGTGTCTAG TAGCGGGACC CCCCTACTAC     1080

GAAGGGGTTG CCGTCCTGGG TACCTACTCC AACCATACCT CTGCTCCAGC CAACTGCTCC     1140

GTGGCCTCCC AACACAAGTT GACCCTGTCC GAAGTGACCG GACAGGGACT CTGCATAGGA     1200

GCAGTTCCCA AAACACATCA GGCCCTATGT AATACCACCC AGACAAGCAG TCGAGGGTCC     1260

TATTATCTAG TTGCCCCTAC AGGTACCATG TGGGCTTGTA GTACCGGGCT TACTCCATGC     1320

ATCTCCACCA CCATACTGAA CCTTACCACT GATTATTGTG TTCTTGTCGA ACTCTGGCCA     1380

AGAGTCACCT ATCATTCCCC CAGCTATGTT TACGGCCTGT TTGAGAGATC CAACCGACAC     1440

AAAAGA                                                                1446
```

(2) INFORMATION FOR SEQ ID NO: 3:

(i) SEQUENCE CHARACTERISTICS:
        (A) LENGTH: 453 amino acids
        (B) TYPE:  amino acid
        (C) STRANDEDNESS:
        (D) TOPOLOGY:  linear (ii) MOLECULE TYPE:  protein (ix) FEATURE:
        (A) NAME/KEY:xenotropic gp70 protein (xi) SEQUENCE DESCRIPTION:  SEQ ID NO:3:

```
Met Glu Gly Ser Ala Phe Ser Lys Pro Leu
                5                   10

Lys Asp Lys Ile Asn Pro Trp Gly Pro Leu
               15                   20

Ile Val Met Gly Ile Leu Val Arg Ala Gly
               25                   30

Ala Ser Val Gln Arg Asp Ser Pro His Gln
               35                   40

Ile Phe Asn Val Thr Trp Arg Val Thr Asn
               45                   50

Leu Met Thr Gly Gln Thr Ala Asn Ala Thr
               55                   60

Ser Leu Leu Gly Thr Met Thr Asp Thr Phe
               65                   70

Pro Lys Leu Tyr Phe Asp Leu Cys Asp Leu
               75                   80

Pro Lys Leu Tyr Phe Asp Leu Cys Asp Leu
               85                   90

Val Gly Asp Tyr Trp Asp Asp Pro Glu Pro
               95                  100

Asp Ile Gly Asp Gly Cys Arg Thr Pro Gly
              105                  110

Gly Arg Arg Arg Thr Arg Leu Tyr Asp Phe
              115                  120

Tyr Val Cys Pro Gly His Thr Val Pro Ile
              125                  130
```

```
Gly Cys Gly Gly Pro Gly Glu Gly Tyr Cys
            135                 140

Gly Lys Trp Gly Cys Glu Thr Thr Gly Gln
            145                 150

Ala Tyr Trp Lys Pro Ser Ser Ser Trp Asp
            155                 160

Leu Ile Ser Leu Lys Arg Gly Asn Thr Pro
            165                 170

Lys Asp Gln Gly Pro Cys Tyr Asp Ser Ser
            175                 180

Val Ser Ser Gly Val Gln Gly Ala Thr Pro
            185                 190

Gly Gly Arg Cys Asn Pro Leu Val Leu Glu
            195                 200

Phe Thr Asp Ala Gly Arg Lys Ala Ser Trp
            205                 210

Asp Ala Pro Lys Val Trp Gly Leu Arg Leu
            215                 220

Tyr Arg Ser Thr Gly Ala Asp Pro Val Thr
            225                 230

Arg Phe Ser Leu Thr Arg Gln Val Leu Asn
            235                 240

Val Gly Pro Arg Val Pro Ile Gly Pro Asn
            245                 250

Pro Val Ile Thr Asp Gln Leu Pro Pro Ser
            255                 260

Gln Pro Val Gln Ile Met Leu Pro Arg Pro
            265                 270

Pro His Pro Pro Ser Gly Thr Val Ser
            275                 280

Met Val Pro Gly Ala Pro Pro Ser Gln
            285                 290

Gln Pro Gly Thr Gly Asp Arg Leu Leu Asn
            295                 300

Leu Val Glu Gly Ala Tyr Gln Ala Leu Asn
            305                 310

Leu Thr Ser Pro Asp Lys Thr Gln Glu Cys
            315                 320

Trp Leu Cys Leu Val Ser Gly Pro Pro Tyr
            325                 330

Tyr Glu Gly Val Ala Val Leu Gly Thr Tyr
            335                 340

Ser Asn His Thr Ser Ala Pro Ala Asn Cys
            345                 350

Ser Val Ala Ser Gln His Lys Leu Thr Leu
            355                 360

Ser Glu Val Thr Gly Gln Gly Leu Cys Val
            365                 370

Gly Ala Val Pro Lys Thr His Gln Ala Leu
            375                 380

Cys Asn Thr Thr Gln Lys Thr Ser Asp Gly
            385                 390

Ser Tyr Tyr Leu Ala Ala Pro Ala Gly Thr
```

```
                   395                 400
Ile Trp Ala Cys Asn Thr Gly Leu Thr Pro
                405                 410

Cys Leu Ser Thr Thr Val Leu Asn Leu Thr
                415                 420

Thr Asp Tyr Cys Val Leu Val Glu Leu Trp
                425                 430

Pro Lys Val Thr Tyr His Ser Pro Asp Tyr
                435                 440

Val Tyr Gly Gln Phe Glu Lys Lys Thr Lys
                445                 450

Tyr Lys Arg
```

(2) INFORMATION FOR SEQ ID NO: 4:

(i) SEQUENCE CHARACTERISTICS:
        (A) LENGTH: 1356 bases
        (B) TYPE: nucleic acid
        (C) STRANDEDNESS: single
        (D) TOPOLOGY: linear (ii) MOLECULE TYPE: viral DNA (xi) SEQUENCE DESCRIPTION: SEQ ID NO:4:

```
GCGACAACTC CTCCAGCCGG AACAGCATG GAAGGTTCAG CGTTCTCAAA ACCCCTTAAA    60
GATAAGATTA ACCCGTGGGG CCCCCTAATA GTTATGGGGA TCTTGGTGAG GGCAGGAGCT   120
TCGGTACAAC GTGACAGCCC TCACCAGATC TTCAATGTTA CTTGGAGAGT TACCAACCTA   180
ATGACAGGAC AAACAGCTAA CGCCACCTCC CTCCTGGGGA CGATGACAGA CACCTTCCCT   240
AAACTATATT TTGACCTGTG TGATTTAGTA GGAGACTACT GGGATGACCC AGAACCCGAT   300
ATTGGGGATG GTTGCCGCAC TCCCGGGGGA AGAAGAAGGA CAAGACTGTA TGACTTCTAT   360
GTTTGCCCCG GTCATACTGT ACCAATAGGG TGTGGAGGGC CGGGAGAGGG CTACTGTGGC   420
AAATGGGGAT GTGAGACCAC TGGACAGGCA TACTGGAAGC CATCATCATC ATGGGACCTA   480
ATTTCCCTTA AGCGAGGAAA CACTCCTAAG GATCAGGGCC CCTGTTATGA TTCCTCGGTC   540
TCCAGTGGCG TCCAGGGTGC CACACCGGGG GGTCGATGCA ACCCCCTGGT CTTAGAATTC   600
ACTGACGCGG GTAGAAAGGC CAGCTGGGAT GCCCCCAAAG TTTGGGGACT AAGACTCTAT   660
CGATCCACAG GGGCCGACCC GGTGACCCGG TTCTCTTTGA CCCGCCAGGT CCTCAATGTA   720
GGACCCCGCG TCCCCATTGG GCCTAATCCC GTGATCACTG ACCAGCTACC CCCATCCCAA   780
CCCGTGCAGA TCATGCTCCC CAGGCCTCCT CATCCTCCTC CTTCAGGCAC GGTCTCTATG   840
GTACCTGGGG CTCCCCCGCC TTCTCAACAA CCTGGGACGG GAGACAGGCT GCTAAATCTG   900
GTAGAAGGAG CCTACCAAGC ACTCAACCTC ACCAGTCCTG ACAAAACCCA AGAGTGCTGG   960
TTGTGTCTGG TATCGGGACC CCCCTACTAC GAAGGGCTTG CCGTCCTAGG TACCTACTCC  1020
AACCATACCT CTGCCCCAGC TAACTGCTCC GTGGCCTCCC AACACAAGCT GACCCTGTCC  1080
GAAGTAACCG GACAGGGACT CTGCGTAGGA GCAGTTCCCA AAACCCATCA GGCCCTGTGT  1140
AATACCACCC AGAAGACGAG CGACGGGTCC TACTATCTGG CTGCTCCCGC CGGGACCATC  1200
TGGGCTTGCA ACACCGGGCT CACTCCCTGC CTATCTACTA CTGTACTCAA CCTCACCACC  1260
GATTACTGTG TCCTGGTTGA GCTCTGGCCA AAGGTAACCT ACCACTCCCC TGATTATGTT  1320
TATGGCCAGT TTGAAAAGAA AACTAAATAT AAAAGA                            1356
```

(2) INFORMATION FOR SEQ ID NO: 5:

(i) SEQUENCE CHARACTERISTICS:
      (A) LENGTH: 201 amino acids
      (B) TYPE: amino acid
      (C) STRANDEDNESS:
      (D) TOPOLOGY: linear (ii) MOLECULE TYPE: protein (ix) FEATURE:
      (A) NAME/KEY:rabbit alpha-1-acid glycoprotein (x) PUBLICATION INFORMATION:
      (A) AUTHORS: Ray, et al.
      (B) TITLE:
      (C) JOURNAL: Biochem. and Biophys. Res. Comm.
      (D) VOLUME: 178
      (E) ISSUE: No. 2
      (F) PAGES: 507-513
      (G) DATE: 1991

(xi) SEQUENCE DESCRIPTION: SEQ ID NO: 5:

```
Met Ala Leu Pro Trp Ala Leu Ala Val Leu
                 5                  10

Ser Leu Leu Pro Leu Leu His Ala Gln Asp
                15                  20

Pro Ala Cys Ala Asn Phe Ser Thr Ser Pro
                25                  30

Ile Thr Asn Ala Thr Leu Asp Gln Leu Ser
                35                  40

His Lys Trp Phe Phe Thr Ala Ser Ala Phe
                45                  50

Arg Asn Pro Lys Tyr Lys Gln Leu Val Gln
                55                  60

His Thr Gln Ala Ala Phe Phe Tyr Phe Thr
                65                  70

Ala Ile Lys Glu Glu Asp Thr Leu Leu Leu
                75                  80

Arg Glu Tyr Ile Thr Thr Asn Asn Thr Cys
                85                  90

Phe Tyr Asn Ser Ser Ile Val Arg Val Gln
                95                  100

Arg Glu Asn Gly Thr Leu Ser Lys His Asp
105                 110

Gly Ile Arg Asn Ser Val Ala Asp Leu Leu
115                 120

Leu Leu Arg Asp Pro Gly Ser Phe Leu Leu
125                 130

Val Phe Phe Ala Gly Lys Glu Gln Asp Lys
135                 140

Gly Met Ser Leu Tyr Thr Asp Lys Pro Lys
145                 150

Ala Ser Thr Glu Gln Leu Glu Glu Phe Tyr
155                 160

Glu Ala Leu Thr Cys Leu Gly Met Asn Lys
165                 170

Thr Glu Val Val Tyr Thr Asp Trp Thr Lys
175                 180

Asp Leu Cys Glu Pro Leu Glu Lys Gln His
185                 190
```

```
Glu Glu Glu Arg Lys Lys Glu Lys Ala Glu
195                 200

Ser
```

(2) INFORMATION FOR SEQ ID NO:6:

(i) SEQUENCE CHARACTERISTICS:
        (A) LENGTH: 759 bases
        (B) TYPE: nucleic acid
        (C) STRANDEDNESS: single
        (D) TOPOLOGY: linear (ii) MOLECULE TYPE: genomic DNA (x) PUBLICATION INFORMATION:
        (A) AUTHORS: Ray, et al.
        (B) TITLE:
        (C) JOURNAL: Biochem. and Biophys. Res. Comm.
        (D) VOLUME: 178
        (E) ISSUE: NO. 2
        (F) PAGES: 507-513
        (G) DATE: 1991

(xi) SEQUENCE DESCRIPTION: SEQ ID NO:6:

```
AGCTCTGCCT GGCTCCAGCG CCTCTGTGTC TCAGCATGGC CCTGCCCTGG GCCCTCGCCG      60
TCCTGAGCCT CCTCCCTCTG CTGCATGCCC AGGACCCAGC GTGTGCCAAC TTCTCGACCA     120
GCCCTATCAC CAATGCCACC CTGGACCAGC TCTCCCACAA GTGGTTTTTT ACCGCCTCGG     180
CCTTCCGGAA CCCCAAGTAC AAGCAGCTGG TGCAGCATAC CCAGGCGGCC TTTTTCTACT     240
TCACCGCCAT CAAAGAGGAG GACACCTTGC TGCTCCGGGA GTACATAACC ACGAACAACA     300
CGTGCTTCTA TAACTGCAGC ATCGTGAGGG TCCAGAGAGA GAATGGGACC CTCTCCAAAC     360
ACGACGGCAT ACGAAATAGC GTGGCCGACC TGCTGCTCCT CAGGGACCCC GGGAGCTTCC     420
TCCTCGTCTT CTTCGCTGGG AAGGAGCAGG ACAAGGGAAT GTCCTTCTAC ACCGACAAGC     480
CCAAGGCCAG CCCGGAACAA CTGGAAGAGT TCTACGAAGC CCTCACGTGC TGGGCATGA     540
ACAAGACGGA AGTCGTCTAC ACTGACTGGA CAAAGGATCT GTGCGAGCCG CTGGAGAAGC     600
AACACGAGGA GGAGAGGAAG AAGGAAAAGG CAGAGTCATA GGGCACAGCA CCGGCTCCGG     660
GACTCGGGGC CCACCCCCTG CACCTGCCTT TTTGTTTGTT TTGTAAATCT CTGTTCTTTC     720
CCATGGTTGC ATCAATAAAA CTGCTGGACC AGTAAAAAA                            759
```

(2) INFORMATION FOR SEQ ID NO: 7:

(i) SEQUENCE CHARACTERISTICS:
        (A) LENGTH: 196 amino acids
        (B) TYPE: amino acid
        (C) STRANDEDNESS:
        (D) TOPOLOGY: linear (ii) MOLECULE TYPE: protein (ix) FEATURE:
        (A) NAME/KEY: ecotropic p15E protein.

(xi) SEQUENCE DESCRIPTION: SEQ ID NO: 7:

```
Glu Pro Val Ser Leu Thr Leu Ala Leu Leu
                5                   10

Leu Gly Gly Leu Thr Met Gly Gly Ile Ala
                15                  20

Ala Gly Ile Gly Thr Gly Thr Thr Ala Leu
                25                  30

Met Ala Thr Gln Gln Phe Gln Gln Leu Gln
```

```
                    35                  40
Ala Ala Val Gln Asp Asp Leu Arg Glu Val
                45                  50

Glu Lys Ser Ile Ser Asn Leu Glu Lys Ser
                55                  60

Leu Thr Ser Leu Ser Glu Val Val Leu Gln
                65                  70

Asn Arg Arg Gly Leu Asp Leu Leu Phe Leu
                75                  80

Lys Glu Gly Gly Leu Cys Ala Ala Leu Lys
                85                  90

Glu Glu Cys Cys Phe Tyr Ala Asp His Thr
                95                 100

Gly Leu Val Arg Asp Ser Met Ala Lys Leu
               105                 110

Arg Glu Arg Leu Asn Gln Arg Gln Lys Leu
               115                 120

Phe Glu Ser Thr Gln Gly Trp Phe Glu Gly
               125                 130

Leu Phe Asn Arg Ser Pro Trp Phe Thr Thr
               135                 140

Leu Ile Ser Thr Ile Met Gly Pro Leu Ile
               145                 150

Val Leu Leu Met Ile Leu Leu Phe Gly Pro
               155                 160

Cys Ile Leu Asn Arg Leu Val Gln Phe Val
               165                 170

Lys Asp Arg Ile Ser Val Val Gln Ala Leu
               175                 180

Val Leu Thr Gln Gln Tyr His Gln Leu Lys
               185                 190

Pro Ile Glu Tyr Glu Pro
               195

(2) INFORMATION FOR SEQ ID NO:8:

(i) SEQUENCE CHARACTERISTICS:
        (A) LENGTH:  176 amino acids
        (B) TYPE:  amino acid
        (C) STRANDEDNESS:
        (D) TOPOLOGY:  linear (ii) MOLECULE TYPE:  protein (ix) FEATURE:
        (A) NAME/KEY:  HTLV-I p21 protein (x) PUBLICATION INFORMATION:
        (A) AUTHORS:  Malik, et al.
        (B) TITLE:
        (C) JOURNAL:  J. Gen. Virol.
        (D) VOLUME:  69
        (E) ISSUE:
        (F) PAGES:  1695-1710
        (G) DATE:  1988

(xi) SEQUENCE DESCRIPTION:  SEQ ID NO:8:

Ala Val Pro Val Ala Val Trp Leu Val Ser
                 5                  10

Ala Leu Ala Met Gly Ala Gly Val Ala Gly
                15                  20
```

-continued

```
Arg Ile Thr Gly Ser Met Ser Leu Ala Ser
                25                  30

Gly Lys Ser Leu Leu His Glu Val Asp Lys
                35                  40

Asp Ile Ser Gln Leu Thr Gln Ala Ile Val
                45                  50

Lys Asn His Lys Asn Leu Leu Lys Ile Ala
                55                  60

Gln Tyr Ala Ala Gln Asn Arg Arg Gly Leu
                65                  70

Asp Leu Leu Phe Trp Glu Gln Gly Gly Leu
                75                  80

Cys Lys Ala Leu Gln Glu Gln Cys Cys Phe
                85                  90

Leu Asn Ile Thr Asn Ser His Val Ser Ile
                95                  100

Leu Gln Glu Arg Pro Pro Leu Glu Asn Arg
                105                 110

Val Leu Thr Gly Trp Gly Leu Asn Trp Asp
                115                 120

Leu Gly Leu Ser Gln Trp Ala Arg Glu Ala
                125                 130

Leu Gln Thr Gly Ile Thr Leu Val Ala Leu
                135                 140

Leu Leu Leu Val Ile Leu Ala Gly Pro Cys
                145                 150

Ile Leu Arg Gln Leu Arg His Leu Pro Ser
                155                 160

Arg Val Arg Tyr Pro His Tyr Ser Leu Ile
                165                 170

Asn Pro Glu Ser Ser Leu
                175
```